(12) United States Patent
Bakel Van et al.

(10) Patent No.: US 7,442,811 B2
(45) Date of Patent: Oct. 28, 2008

(54) PROCESS FOR THE PREPARATION OF DIOXANE ACETIC ACID ESTERS

(75) Inventors: Hermanus Carolus Catherina Karel Bakel Van, Helden (NL); Dominique Monique Charles Callant, Houthalen (BE); Jacob Hermanus Mattheus Hero Kooistra, Venlo (NL); Peter Johannes Dominicus Maas, Puth (NL)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 10/518,164

(22) PCT Filed: Jun. 12, 2003

(86) PCT No.: PCT/NL03/00435

§ 371 (c)(1),
(2), (4) Date: Jul. 25, 2005

(87) PCT Pub. No.: WO03/106447

PCT Pub. Date: Dec. 24, 2003

(65) Prior Publication Data

US 2006/0122407 A1    Jun. 8, 2006

(30) Foreign Application Priority Data

Jun. 17, 2002    (EP) ................... 02100715

(51) Int. Cl.
C07D 319/06    (2006.01)
(52) U.S. Cl. ..................................... 549/375
(58) Field of Classification Search ................ 549/375
See application file for complete search history.

(56) References Cited

U.S. PATENT DOCUMENTS

| | | | |
|---|---|---|---|
| 3,325,466 A | 6/1967 | Anderson et al. | |
| 5,278,313 A | 1/1994 | Thottathil et al. | |
| 5,457,227 A | 10/1995 | Thottathil et al. | |
| 5,594,153 A | 1/1997 | Thottathil et al. | |
| 6,278,001 B1 | 8/2001 | Solladie et al. | |
| 6,331,641 B1 | 12/2001 | Taoka et al. | |
| 6,340,767 B1 | 1/2002 | Nishiyama et al. | |
| 6,344,569 B1 | 2/2002 | Mitsuda et al. | |
| 6,784,171 B2 | 8/2004 | Taylor et al. | |
| 6,844,437 B1 | 1/2005 | Taylor et al. | |
| 6,870,059 B2 | 3/2005 | Kooistra et al. | |
| 2006/0050044 A1 | 3/2006 | Ikeda | |

FOREIGN PATENT DOCUMENTS

| EP | 0 862 646 | 9/1998 |
|---|---|---|
| EP | 1 024 139 | 8/2000 |
| GB | 885516 | 12/1961 |
| JP | 04266879 | 9/1992 |
| WO | WO-91/13876 | 9/1991 |
| WO | WO-93/06235 | 4/1993 |
| WO | WO 93/08823 | 5/1993 |
| WO | WO-96/31615 | 10/1996 |
| WO | WO 97/19917 | 6/1997 |
| WO | WO-99/57109 | 11/1999 |
| WO | WO-00/08011 | 2/2000 |
| WO | WO 00/49014 | 8/2000 |
| WO | WO-00/68221 | 11/2000 |
| WO | WO 01/72706 | 10/2001 |
| WO | WO 01/85975 | 11/2001 |
| WO | WO-02/06266 | 1/2002 |
| WO | WO 03/006439 | 1/2003 |
| WO | WO-03/059901 | 7/2003 |
| WO | WO 2004/014872 | 2/2004 |
| WO | WO 2004/054986 | 7/2004 |
| WO | WO 2004/108691 | 12/2004 |
| WO | WO 2004/113314 | 12/2004 |
| WO | WO 2005/023779 | 3/2005 |
| WO | WO 2005/028450 | 3/2005 |
| WO | WO 2005/042522 | 5/2005 |
| WO | WO 2006/040898 | 4/2006 |
| WO | WO 2006/067456 | 6/2006 |

OTHER PUBLICATIONS

Advanced Organic Chemistry, Reactions, Mechanisms and Structure, p. 392 (1992).

(Continued)

*Primary Examiner*—Taylor Victor Oh
(74) *Attorney, Agent, or Firm*—Morgan, Lewis & Bockius LLP

(57) ABSTRACT

Process for the preparation of an ester of formula (1), wherein $R^1$ represents a leaving group, CN, OH or a $COOR^5$ group, $R^3$ and $R^4$ each independently represent a 1-3 C alkyl group, and $R^2$ and $R^5$ each independently represent an ester residue, wherein the corresponding salt with formula (2), wherein M represents H or an alkali (earth) metal in an inert solvent is contacted with an acid chloride forming agent to form the corresponding acid chloride, and the acid chloride is contacted with an alcohol with formula $R^2OH$ in the presence of N-methyl-morpholine. Preferably M represents an alkali metal, and $R^2$ represents an alkyl group, particularly a t.-butyl group. (1), (2)

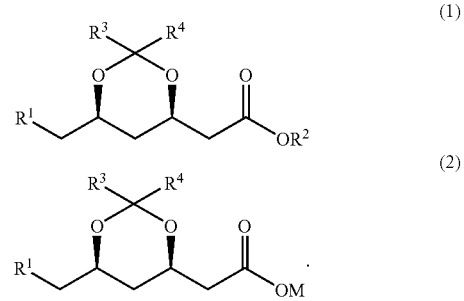

11 Claims, No Drawings

OTHER PUBLICATIONS

Barry et al., "Easy and Efficient Anion Alkylations in Solid-Liquid PTC Conditions," Tetrahedron Letters 23(51):5407-5408 (1982).

Bennett et al., "Methyl (3R)-3-Hydroxyhex-5-enoate as a Precursor to Chiral Mevinic Acid Analogues," J. Chem. Soc. 1:133-140 (1991).

Bram et al., "Anionic Activation by Solid-Liquid Phase Transfer Catalysis Without Solvent: An Improvement in Organic Synthesis," Israel Journal of Chemistry 26:291-298 (1985).

Chevallet, P., et al., "Facile Synthesis of Tert-Butyl Ester of N-Protected Amino Acids with Tert-Butyl Bromide," Tetrahedron Letters, 34(46): 7409-7412 (1993).

Chikara et al., "Preparation of Optically Active 5,6-epoxyhexanoic Acid Esters as Materials for Physiologically Active Substances," Chemical Abstracts 118(11) (1993).

Crowther, G.P., et al., "Esterification of Hindered Alcohols: t-Butyl p-Toluate," Org. Synth., 51:96-100 (1971).

Drugs of the Future, 24(5):511-513 (1999).

Inanaga, J., et al., "A Rapid Esterification by Means of Mixed Anhydride and its Application to Large-ring Lactonization," Bulletin of the Chemical Society of Japan, 52(7):1989-1993 (1979).

Murakami, M., et al., "2,4,6-Tripyridinio-1,3,5-Triazine Trichloride, a New and Mild Esterification Agent for Preparation of Penicillin Esters," Heterocycles, 31(11):2055-2064 (1990).

Murphy, C.F., et al., "Chemistry of Cephalosporin Antibiotics. XVIII. Synthesis of 7-Acyl-3-methyl-cephem-4-carboxylic Acid Esters," J. Org. Chem., 35(7):2429-2430 (1970).

Rayle, H.L., et al., "Development of a Process for Triazine-Promoted Amidation of Carboxylic Acids," Organic Process Research & Development, 3:172-176 (1999).

Sakaki et al., "Lipase-catalyzed Asymmetric Synthesis of 6-(3-Chloro-2-hydroxypropyl)-1,3-dioxin-4-ones and Their Conversion to Chiral 5,6-Epoxyhexanoates," Tetrahedron: Asymmetry 2(5):343-346 (1991).

Takeda, K., et al., "Dicarbonates: Convenient 4-Dimethylaminopyridine Catalyzed Esterification Reagants," Synthesis, 1063-1066 (1994).

Thierry, J., et al., "2-Phenyl Isopropyl and t-Butyl Trichloroacetimidates: Useful Reagents for Ester Preparation of N-Protected Amino acids under Neutral Conditions," Tetrahedron Letters, 39:1557-1560 (1998).

Watanabe, M., et al., "Synthesis and Biological Activity of Methanesulfonamide Pyrimidine-and N-Methanesulfonyl Pyrrole-Substituted 3,5-Dihydroxy-6-heptenoates, a Novel Series of HMG-CoA Reductase Inhibitors," Bioorganic & Medicinal Chemistry, 5(2):437-444 (1997).

Weissenfels, M., et al., "Acetate von Aminosauro-tert-butylestem," Z. Chem., 12(7):264-265 (1972).

Ziegler, F.E., et al., "A Mild Method for the Esterification of Fatty Acids," Synthetic Communications, 9(6):539-543 (1979).

March, Advanced Organic Chemistry: Reactions, Mechanisms, and Structure, 4th ed., John Wiley & Sons, Inc, p. 378 (1992).

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Morrison and Boyd "Alkaline hydrolysis of esters" Lehrbuch der Organischen Chemie, 2nd ed., Verlag Chemie, p. 739 (1978) (Translation enclosed).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

PROCESS FOR THE PREPARATION OF DIOXANE ACETIC ACID ESTERS

RELATED APPLICATIONS

This application is a national stage filing under 35 U.S.C. 371 of International Application PCT/NL03/00435, filed Jun. 12, 2003, which claims priority from European Application No. 02100715.8, filed Jun. 17, 2002 the specifications of each of which are incorporated by reference herein. International Application PCT/NL03/00435 was published under PCT Article 21(2) in English.

The invention relates to a process for the preparation of an ester of formula (1)

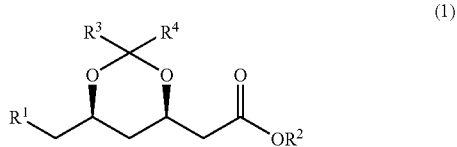

(1)

wherein $R^1$ represents a leaving group, CN, OH or a $COOR^5$ group, $R^3$ and $R^4$ each independently represent a C1-3 alkyl group and $R^2$ and $R^5$ each independently represent an ester residue, wherein the corresponding salt with formula (2)

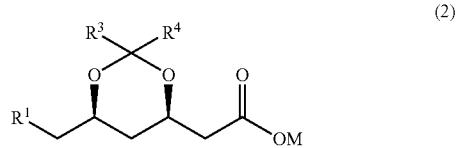

(2)

wherein M represents H or an alkali (earth) metal in an inert solvent is contacted with an acid chloride forming agent to form the corresponding acid chloride, and the acid chloride is contacted with an alcohol with formula $R^2OH$ in the presence of N-methyl morpholine (NMM).

Many processes for the preparation of esters are known in the art, for instance the preparation of esters via the formation of the acid chloride. It was, however, to be expected that such processes would not lead to high yields due to the lack of stability of the present compound under acidic conditions.

It is the object of the invention to provide a process for the preparation of esters with high yield in a robust process, even at large scale and with relatively high concentrations.

Surprisingly it has been found that even sterically hindered esters that are difficult to obtain in esterifications like t-butyl esters of the acid unstable molecules of formula (1), can be obtained in high yield in an easily reproducible process.

With the process according to the invention esters with formula (1) that are unstable under acidic conditions, for instance with pH<4, can be prepared in high yield.

$R^1$ represents a leaving group, CN, OH or a $COOR^5$ group wherein $R^5$ represents an ester residue, for example an alkyl group with for instance 1-6 C-atoms, or an aryl group with for instance 6-12 C-atoms. A leaving group by definition is a group that can easily be replaced, for example a halogen, for instance Cl, Br or I; a tosylate group; a mesylate group; an acyloxy group, with, for instance, 1-6 C-atoms in particular an acetoxy group; a phenacetyloxy group; an alkoxy group with, for instance, 1-6 C-atoms or an (hetero) aryloxy group with, for instance, 6-12 C-atoms. Preferably $R^1$ represents Cl.

$R^2$ represents an ester residue, preferably an alkyl group, for instance an alkyl group with 1-6 C-atoms or an aryl group, for instance an aryl group with 6-12 C-atoms, in particular a methyl, ethyl, propyl, isobutyl or t.butyl group. An important group of esters that can be prepared with the process according to the invention are t.butyl esters.

$R^3$ and $R^4$ each independently represent a C1-C3 alkyl group, for instance a methyl or ethyl group. Preferably $R^3$ and $R^4$ both represent methyl.

M in formula (2) can be chosen from the group of H, alkali metals, for instance lithium, sodium, potassium and alkali earth metals, for instance magnesium or calcium. Preferably M represents sodium or potassium.

The acid chloride forming agent can be chosen from the group of reagents that is generally known as such. Suitable examples of acid chloride forming agents are oxalyl chloride, thionyl chloride, $PCl_3$, $PCl_5$, and $POCl_3$. Preferably the acid chloride forming agent is used in an excess relative to the amount the salt with formula (2), for instance between 1 and 3 equivalents, more preferably between 1.2 and 1.8 equivalents.

If desired, in the acid chloride formation also a catalyst may be present. The amount of catalyst may for instance vary from 0-1, preferably 0-0.5 equivalents, calculated with respect to the amount of salt with formula (2). Higher amounts of catalyst are also possible, but will normally have no extra advantageous effect. Preferably the amount of catalyst, if any, will be between 0.05 and 0.2 equivalents calculated with respect to the salt with formula (2). Suitable catalysts are the catalysts generally know to accelerate acid chloride formation, for instance dimethylformamide (DMF) and N-methylpyrrolidone (NMP).

The conversion of the acid chloride into the ester with formula (1) is carried out in the presence of an alcohol with formula $R^2OH$. The amount of alcohol with formula $R^2OH$ is not very critical and preferably is between 1 and 15 equivalent calculated with respect to the amount of salt with formula (2), more preferably between 2 and 13, most preferably between 3 and 6. Surprisingly it has been found that even t.-butyl esters can be prepared with high yield using a relatively low amount of t.-butyl alcohol.

The conversion of the acid chloride into the ester with formula (1) is carried out in the presence of NMM. In practice a small amount of NMM, efficient to catch eventually remaining free HCl, for instance 1.5 to 2.5, preferably 1.8 to 2.0 equivalents calculated with respect to the amount of salt with formula (2) is applied. When a large excess of acid chloride forming agent is used, preferably higher amounts of NMM are used, and when a lower excess of acid chloride forming agent is used, preferably lower amounts of NMM are used.

The acid chloride formation reaction preferably is carried out at a temperature between −30° and 60° C., more preferably between 20 and 50° C. The conversion of the acid chloride into the ester with formula (1) preferably is carried out at a temperature between 20 and 80° C., more preferably between 20 and 50° C.

The process of the present invention may be carried out in one step. Preferably first the salt with formula (2) is converted into the corresponding acid chloride, and subsequently the acid chloride is contacted with the alcohol with formula $R^2OH$ and NMM. In a particularly preferred embodiment the acid chloride formed is quenched with NMM and the alcohol with formula $R^2OH$.

The product with formula 1, wherein $R^1$ represents a leaving group may subsequently be converted into the corresponding compound wherein $R^1$ represents an acyloxy group.

This can be achieved in a manner known per se, for instance by reaction with an acyloxylating agent for instance a carboxylic or sulphonic acid, a quaternary ammonium or phosphonium salt, a carboxylic or sulphonic acid quaternary ammonium or phosphonium salt or a combination thereof. Preferably a combination of a quaternary phosphonium salt and a carboxylic or sulphonic acid salt is used as the acyloxylating agent.

Subsequently the compound with formula 1, wherein $R^1$ represents an acyloxy group can be converted in the corresponding compound wherein $R^1$ represents a hydroxy group, for instance by subjecting it to solvolysis in the presence of a base. Suitable bases are, for instance, alkali (earth) metal hydroxides or carbonates or organic bases, for instance alkali (earth) metal carboxylic acids, for instance acetates, ammonia, pyridines, amines, for instance triethylamine and the like.

The invention will be elucidated by the following examples.

EXAMPLE I 1864 g of an aqueous solution of the (4R-cis)-(6-chloromethyl)-2,2-dimethyl-1,3-dioxane-4-yl-acetic acid, sodium salt (3.31 moles) and 4.8 L of toluene were mixed and water was removed by azeotropic distillation under reduced pressure. Subsequently, 870 g of fresh toluene were added and removed by distillation. To the obtained suspension was added 33.4 g of NMP. Then 588 g of oxalyl chloride were added while maintaining the temperature at 20° C. The resulting mixture was stirred for 6 hours at 20-25° C. and then slowly added to a mixture of 979 g of t.-butanol and 836 g of N-methyl morpholine. After stirring for 1 hour, 3966 g of an 8% (w/w) aqueous NaOH solution was added and the resulting mixture stirred for 1.5 hours at 40° C. After washing the organic phase with 3300 g of water, 3064 g of a toluene solution of the desired t.-butyl ester was obtained, corresponding to 751 g (81%) of product.

EXAMPLE II

In a 100 ml HEL Vessel with 4 blade stirrer 8.0 g (4R-cis)-(6-chloromethyl)-2,2-dimethyl-1,3-dioxane-4-yl-acetic acid, sodium salt (92.4%; 30 mmol) was suspended in 41 g toluene and 0.3 g NMP (3 mmol). In 1 h 4.5 g (36 mmol) oxalylchloride was dosed at a temperature of 15-20° C. The reaction mixture (50 g) was stirred for 2.5 hours. The reaction mixture was split into 2 parts: Part A (23.83 g) and part B (24.25 g). Part A of the reaction mixture was dosed during 1 h. to a mixture of 22.2 g (20 eq.) t.-butanol and 3.0 g (2 eq.) NMM at 25° C. The reaction mixture was stirred overnight and analyzed by GC. The yield of the t.-butyl ester was 88%.

EXAMPLES III-V

Following the same procedure as described in Example I, the ethyl, isopropyl and n-hexyl esters, respectively, are prepared wherein instead of 4 eq. butanol, now 4 eq. ethanol, 4 eq. isopropanol and 4 eq. n-hexanol, respectively is used. The yield of the desired ethyl, isopropyl and n-hexyl ester was 89 mol %, 88 mol % and 84 mol % respectively, calculated with respect to the sodium salt starting material.

EXAMPLE VI

A mixture of 35.0 g of t-butyl (4R-cis)-(6-chloromethyl)-2,2-dimethyl-1,3-dioxane-4-yl-acetate, 14.8 g of tetrabutyl phosphonium bromide, 16.0 g of potassium acetate and 5.9 g of toluene were heated to 105° C. under reduced pressure. After 22 hours at this temperature the reaction mixture was cooled to ambient temperature after which 400 g of heptane and 350 g of water were added. The organic phase was washed with 150 g of water and subsequently treated with 3.0 g of activated carbon. After filtration of the carbon, the solution was concentrated and subsequently cooled to −10° C. after which crystallised product was isolated by means of filtration. Yield 24.9 g (76%) of a white crystalline material.

The invention claimed is:

1. A process for the preparation of an ester of formula (1),

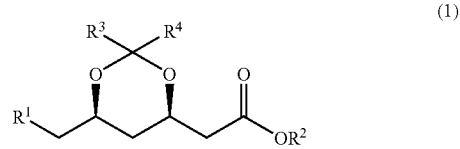

(1)

wherein
  $R^1$ represents a leaving group, CN, OH or a $COOR^5$ group;
  $R^3$ and $R^4$ each independently represent a 1-3C alkyl group; and
  $R^2$ and $R^5$ each independently represent a 1-6C alkyl group or 6-12C aryl group, comprising contacting the corresponding compound of formula (2),

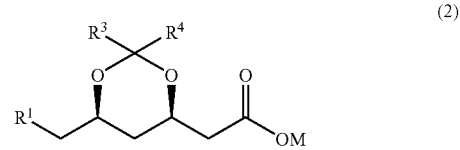

(2)

wherein
  M represents H or an alkali or alkaline earth metal, with an acid chloride forming agent in an inert solvent to form the corresponding acid chloride, and contacting the acid chloride with an alcohol of formula $R^2OH$ in the presence of N-methyl-morpholine.

2. The process according to claim 1, wherein M represents an alkali metal.

3. The process according to claim 1, wherein $R^2$ represents an alkyl group.

4. The process according to claim 3, wherein $R^2$ represents a t-butyl group.

5. The process according to claim 1, wherein the acid chloride forming agent is oxalyl chloride.

6. The process according to claim 1, wherein the acid chloride formation is performed in the presence of a catalyst selected from the group consisting of dimethylformamide (DMF) and N-methylpyrrolidone (NMP).

7. The process according to claim 1, wherein the amount of alcohol of formula $R^2OH$ is between 3 and 6 equivalents calculated with respect to the amount of salt with formula (2).

8. The process according to claim 1, wherein
  the compound of formula (2) is converted into the corresponding acid chloride and subsequently,
  the acid chloride is contacted with the alcohol of formula $R^2OH$ and N-methyl-morpholine.

9. The process according to claim 8, wherein the acid chloride is quenched with the alcohol of formula $R^2OH$ and N-methyl-morpholine.

10. The process according to claim 1, further comprising converting the ester of formula (1) wherein $R^1$ represents a leaving group, into the corresponding ester of formula (1) wherein $R^1$ represents an acyloxy group.

11. The process according to claim 10, wherein
  the ester of formula (1), wherein $R^1$ represents an acyloxy group, is prepared and subsequently,
  the ester of formula (1) is converted into the corresponding compound with formula (1) wherein $R^1$ represents OH.

* * * * *